(12) United States Patent
Satake et al.

(10) Patent No.: US 6,208,420 B1
(45) Date of Patent: Mar. 27, 2001

(54) METHOD AND APPARATUS FOR ESTIMATING QUALITY OF GRAINS

(75) Inventors: Satoru Satake, Tokyo; Yukio Hosaka, Hiroshima; Hideharu Maruyama, Hiroshima; Nobuhiko Nakamura, Hiroshima; Nobuharu Yagishita, Hiroshima, all of (JP)

(73) Assignee: Satake Corporation, Tokyo (JP)

( * ) Notice: Subject to any disclaimer, the term of this patent is extended or adjusted under 35 U.S.C. 154(b) by 0 days.

(21) Appl. No.: 09/501,272

(22) Filed: Feb. 9, 2000

(30) Foreign Application Priority Data

Mar. 2, 1999 (JP) .................................................. 11-054270

(51) Int. Cl.[7] .................................................. G01N 21/55
(52) U.S. Cl. .................... 356/432; 356/445; 250/339.07; 250/339.11
(58) Field of Search .................................... 356/445, 446, 356/447, 448, 402, 419, 432; 250/339.07, 339.1, 339.11, 339.12, 341.8, 358.1, 910

(56) References Cited

U.S. PATENT DOCUMENTS

| 4,084,905 | * | 4/1978 | Schreiber et al. . | |
| 4,752,689 | * | 6/1988 | Satake | 356/446 |
| 4,800,280 | * | 1/1989 | Satake | 250/339 |
| 4,806,764 | * | 2/1989 | Satake | 250/58.1 |
| 5,034,609 | * | 7/1991 | Satake et al. | 250/339 |
| 5,835,206 | * | 11/1998 | Tragesser | 356/72 |
| 6,100,526 | * | 8/2000 | Mayes | 250/339.11 |

* cited by examiner

*Primary Examiner*—Hoa Q. Pham
(74) *Attorney, Agent, or Firm*—Fish & Richardson, PC

(57) ABSTRACT

A method and an apparatus are provided for estimating a quality of grains to be harvested from a grain plant in the future, during a growth period prior to the harvesting. The method comprises the step for establishing a quality conversion coefficient for estimating a specific quality of grains after the harvesting based on absorbencies relating to the specific quality of the grains obtained by irradiating light having predetermined wavelength regions on a leaf of a grain plant in growth at a predetermined time during the growth period of the grain plant and the specific quality obtained from the same grains after the harvesting, and the step for estimating the quality of the grains to be harvested in the future based on said quality conversion coefficient and absorbencies relating to said specific quality obtained from a leaf of the grain plant presently growing at the predetermined time. The measurement for estimating the quality of the grains can be carried out in an easy and simple manner during the growth of grain plants.

8 Claims, 5 Drawing Sheets

METHOD AND APPARATUS FOR ESTIMATING QUALITY OF GRAINS

BACKGROUND OF THE INVENTION (1) Field of the Invention

The present invention relates to a method and an apparatus for estimating the quality of grains, and more particularly to a method and an apparatus with which the quality of the grains after the harvesting can be estimated during the growth of the grain plant prior to the harvesting.

(2) Description of the Related Art

In respect of the rice, it is already known to estimate the amount of protein content in the final brown rice from the biological data obtained before the harvesting period. For example, there has been a disclosure wherein the protein content rate of the brown rice is estimated from the leaf blade nitrogen content rate at the full heading time (disclosed in Ninth non-destructive measurement symposium, November 1993, by Kansai Branch of Nihon Food Product Industry Association; and in Nutrition diagnosis of rice plant by near infrared ray spectral of a fresh leaf, by Keisuke Yoshimatsu, Agricultural Product Processing Study of Yamaguchi Agricultural Experimental Laboratory). However, according to the disclosed technique; the leaf blade was chemically analyzed for preparing an estimation formula, and it was inevitable to consume the time for the preparation of the estimation formula. Also, when the correlation between the leaf blade from the stalk of the given rice plant and the brown rice harvested from the same is observed, since the leaf blade had to be cut from the stalk and used for the chemical analysis, and since the brown rice had to be harvested from the rice plant from which the leaf blade used for the chemical analysis was missing after the chemical analysis, it could not be denied that there would be a shortage in the component or composition produced by the photosynthesis. To prepare the estimation formula from the leaf blade nitrogen content rate and the amount of the harvested brown rice obtained as above will become a cause for lowering the precision.

For estimating the protein content rate in the wheat grains, there is a disclosed example for estimating the protein content rate in the matured grains based on the protein content rate in the immatured grains 30 days before the harvesting (The journal of agriculture, Victoria, May 1963). The disclosure relates to a method of estimating the protein content rate by chemical analysis of the matured particle based on the protein content rate by chemical analysis of the immatured particle. This method requires time for preparing the estimation formula and, since the stalk of the same wheat as that used for the immatured particle is taken and used for the analysis of the matured particle, a shortage in the component or composition is caused and this becomes a cause for the lowering of the precision for the same reason as for the rice plant as explained above. Also, in the case of wheat, since the plant grows in a dried field, there does not exist, unlike with the rice plant which grows in a paddy field, a damper mechanism in which the weather and the fertilization are standardized by water. For this reason, the wheat plant is under the conditions in which the weather conditions such as the duration of sunshine and the accumulated temperature directly affect through the soil so that, even when a biological data for a certain one period before the harvesting is obtained, there is a possibility that the growth estimation curve changes drastically by the subsequent environmental changes. Therefore, as compared with rice, it is extremely difficult to estimate the protein content amount of the matured wheat particle.

SUMMARY OF THE INVENTION

An object of the present invention, therefore, is to overcome the problems existing in the prior art, and to provide a method and an apparatus for estimating the quality of grains, in which during the growth of the plant, in order to conduct the estimation of quality precisely and speedily, the measurement can be carried out in an easy and simple manner. The invention provides, for this reason, the method and the apparatus for preparing the estimation formula which save time and labor. Also, the precision of the growth estimation curve can be enhanced even when the estimation curve is apt to be changed easily as in the wheat.

According to the invention, at the predetermined time during the growth period of a grain plant, the quality conversion coefficient for estimating the specific quality after the harvesting is determined from the absorbency relating to the specific quality of the grain obtained by irradiating light on a leaf of a grain plant in growth and the specific quality of the grains after the harvesting. Then, it is so arranged that, at the specific time during the presently growing period, the quality of the grain to be harvested in the future be estimated from the absorbency relating to the specific quality obtained from the plant leaf and the quality conversion coefficient. In this connection, since the absorbency is measured directly from the leaf of the plant growing, the leaf is neither cut nor damaged so that, without damage to the leaf, the subsequent growth up to the harvesting is not affected.

Also, it is so arranged that, the second quality conversion coefficient is determined from the absorbencies obtained at a plurality of predetermined times during the growth and the specific quality after the harvesting, and the quality of the grain to be harvested is estimated from the absorbencies obtained at the plurality of times from the leaf of the grains presently in growth and the second quality conversion coefficient. In this connection, since the quality conversion coefficient which takes into account the absorbencies of the plurality of times obtained from the plant leaf can be determined, the precision of the estimation of the plant which is apt to be influenced by the environments such as soil and weather is enhanced.

When the specific quality is related to the amount of protein content, it is possible to estimate the quality of majority of grains and, in the case of rice, the amount of the protein relates to the taste and the yield, and the yield is increased but the taste is lowered when the amount of protein is large. On the other hand, since it is known that the yield is decreased but the taste is good when the protein is small, the amount of protein serves as a definite parameter for estimating the quality. With respect to wheat and barley, especially wheat, the amount of protein is known as having high correlation with gluten, so that, by knowing the amount of the protein content, the quality of wheat and barley can be estimated. The qualities of the grains estimated based on the different predetermined times are displayed simultaneously so that the qualities estimated respectively at the different predetermined times can be visually observed and grasped. The differences in the qualities estimated at the different times which are observed visually can be regarded as representing degrees of precision in the quality estimation so that it is possible to know as an experimental value the best time for conducting the measurement in a particular plant.

BRIEF DESCRIPTION OF THE DRAWINGS

The above and other objects, features and advantages of the present invention will be apparent from the following description of preferred embodiments of the invention explained with reference to the accompanying drawings, in which.

PREFERRED EMBODIMENTS OF THE INVENTION

Figure 1:
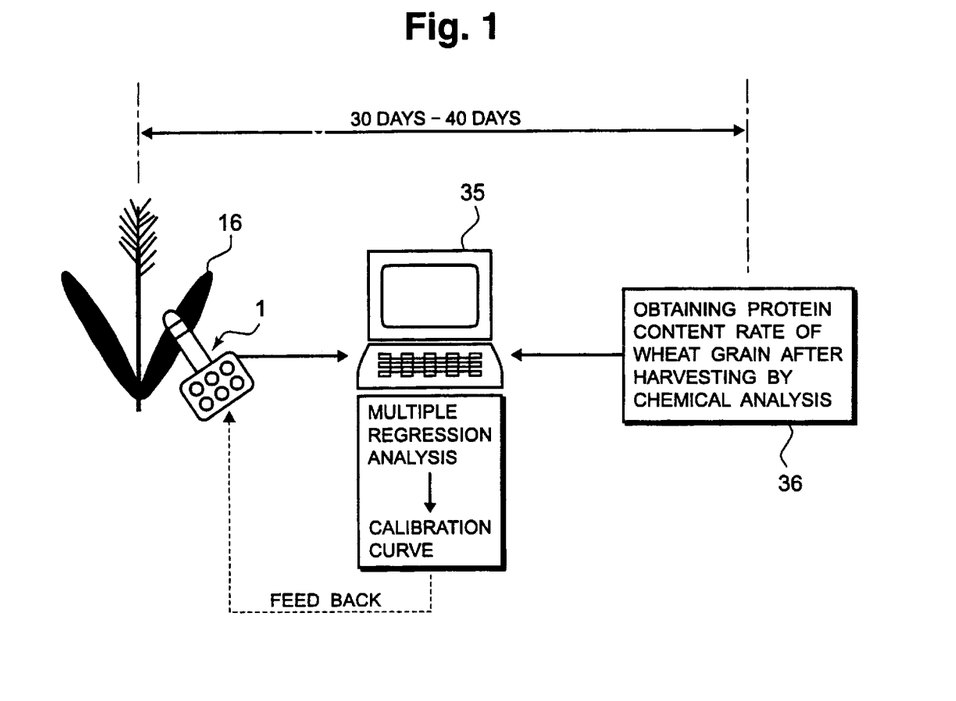
FIG. 1 is a conception diagram for preparing a calibration curve for estimating the quality of grains.

A preferred embodiment of the invention is explained with reference to FIG. 1. With respect to the wheat among various kinds of grains, the specific quality thereof is explained with a protein content rate therein as an example. Based on the absorbency obtained by an absorbency measurement device 1 by irradiating light of specific wavelength regions on a leaf 16 of the wheat plant at a predetermined time of the wheat during the growth, for example, 30 days prior to the harvesting, and on the protein content rate of the wheat grain after the harvesting obtained by chemical analysis 36, the multiple regression analysis is conducted by a personal computer 35 using the protein content rate as an objective variable and the absorbency as an explanatory variable. That is:

$$N1=F0+X1 \cdot F1+X2 \cdot F2+ \ldots +Xn \cdot Fn$$

wherein, $F0 \sim Fn$ are constants, $X1 \sim Xn$ are absorbencies of the leaves of the wheat 30 days prior to the harvesting, and N1 is a protein content rate of the wheat to be harvested.

Assuming that the above formula holds, the absorbencies X of the leaves 30 days prior to the harvesting, and the protein content rate N which is the value of the chemical analysis of the wheat grain after harvesting of which the leaves were measured for the absorbencies, result in:

$$N1=F0+X11 \cdot F1+X12 \cdot F2+ \ldots +X1n \cdot Fn$$
$$N2=F0+X21 \cdot F1+X22 \cdot F2+ \ldots +X2n \cdot Fn$$
$$Nm=F0+Xm1 \cdot F1+Xm2 \cdot F2+ \ldots +Xmn \cdot Fn$$

By subjecting the resulting values to the multiple regression analysis, and seeking $F0 \sim Fn$, the following derives:

$$N=F0+X1 \cdot F1+X2 \cdot F2+ \ldots +Xn \cdot Fn+C \tag{1}$$

wherein, $F0 \sim Fn$ are constants, $X1 \sim Xn$ are absorbencies of the leaves of the wheat 30 days prior to the harvesting, C is a compensating value, and N is an estimation value of a protein content rate of the wheat to be harvested.

Thus, when the absorbencies X of the leaves 30 days before the harvesting of the wheat presently in growth is measured, it is possible to estimate the protein content rate N of the wheat to be harvested.

As above, the measurement of the absorbency of the leaf 30 days prior to the harvesting during the growth can be carried out easily and simply by the portable measurement device 1 equipped with a light source and a light receiving section. In this way, since it is not necessary to cut off the leaf for conducting the measurement, the growth of the plant thereafter is not affected. The chemical analysis of the wheat particle after the harvesting requires a considerable time, but this analysis is made on the wheat particle harvested after it has completely grown without being affected by external causes such as the cutting off of the leaf for purposes of the measurement of the leaf, the reliability of the protein content rate of the wheat particle thus obtained by the chemical analysis is high. The quality conversion coefficient (hereinafter referred to as a "calibration curve") thus determined under the above conditions may preferably be prepared on a field-to-field basis or a variety-to-variety basis. The calibration curve is stored in a memory section of the absorbency measurement device 1 explained later. After the calibration curve is adapted to that suited to an appropriate field or variety, the leaf blade absorbency 30 days prior to the harvesting is measured, and the protein content tent rate of the wheat particle after the harvesting can be estimated prior to the actual harvesting. It is possible to prepare the calibration curve by measuring the absorbency of the leaf of plant 40 days prior to the harvesting instead of 30 days prior thereto.

In the growth of the wheat, the weather conditions such as the duration of sunshine and the accumulated temperature affect largely so that, even when a biological data for a certain one period before the harvesting is obtained, the growth estimation curve changes drastically by the subsequent environmental changes. Thus, it is preferred that the absorbency measurement be conducted a plurality of times during the 30 days–40 days prior to the harvesting. For example, if the absorbency has been obtained by conducting the measurement twice, that is, 40 days and 30 days prior to the harvesting, the following derives:

$$N1=F0+X401 \cdot F401+X402 \cdot F402+ \ldots +X40n \cdot F40n+X301 \cdot F301+X302 \cdot F302+ \ldots +X30n \cdot F30n$$

wherein, $F0 \sim Fn$ are constants, $X401 \sim X40n$ are absorbencies of the leaves of the wheat 40 days prior to the harvesting, $X301 \sim X30n$ are absorbencies of the leaves of the wheat 30 days prior to the harvesting, and N1 is a protein content rate of the wheat to be harvested.

Assuming that the above formula holds, the absorbencies X30 of the leaves 30 days prior to the harvesting, the absorbencies X40 of the leaves 40 days prior to the harvesting, and the protein content rate N which is the value of the chemical analysis of the wheat grain after harvesting, of which the leaves were measured for the absorbencies, result in:

$$N1 = F0 + X4011 \cdot F401 + X4012 \cdot F402 + \ldots + X401n \cdot F40n + X3011 \cdot F301 + X3012 \cdot F302 + \ldots + X301n \cdot F30n$$

$$N2 = F0 + X4021 \cdot F401 + X4022 \cdot F402 + \ldots + X402n \cdot F40n + X3021 \cdot F301 + X3022 \cdot F302 + \ldots + X302n \cdot F30n$$

$$Nm = F0 + X40m1 \cdot F401 + X40m2 \cdot F402 + \ldots + X40mn \cdot F40n + X30m1 \cdot F301 + X30m2 \cdot F302 + \ldots + X30mn \cdot F30n$$

By subjecting the resulting values to the multiple regression analysis, and seeking F0, F401~F40n and F301~F30n, the following derives:

$$N = F0 + X401 \cdot F401 + X402 \cdot F402 + \ldots + X40n \cdot F40n + X301 \cdot F301 + X302 \cdot F302 + \ldots + X30n \cdot F30n + C \qquad (2)$$

wherein, F0, F401~F40n, and F301~F30n are constants, X401~X40n are absorbencies of the leaves of the wheat 40 days prior to the harvesting, X301~X30n are absorbencies of the leaves of the wheat 30 days prior to the harvesting, C is a compensating value.

Thus, by estimating the absorbencies X of the leaves 40 days and 30 days prior to the harvesting of the wheat currently in growth, it is made possible to estimate the protein content rate N of the wheat to be harvested. Here, the predetermined times have been explained as being two times, 40 days and 30 days prior to the harvesting, but the predetermined times may be more than two times. If the calibration curve is prepared by increasing the number of the predetermined times appropriately, thus avoiding complexity, and the absorbency of the leaf is measured based on such calibration curve, the estimation precision can be further enhanced.

Where both the Formula (1) and the Formula (2) or one of them which are the calibration curves determined as above are stored in the absorbency measurement device 1, if, according to the explanatory variables used in the calibration curve stored in the absorbency measurement device 1, the Formula (1), for example, has been stored and the absorbency of the leaf of the wheat 30 days prior to the harvesting is measured, the protein content rate which represents the quality of the wheat at the time of the harvesting is calculated and displayed on the spot. Further, if the Formula (2) has been stored, and the absorbency of the leaf of the wheat is measured twice, 40 days and 30 days prior to the harvesting, and if the measurement 30 days prior to the harvesting is performed, the protein content rate which represents the quality of the wheat at the time of the harvesting is calculated and displayed on the spot. Therefore, the producer's side can confirm the quality of the wheat to be produced, and can present it to the buyer's side before the harvesting. After confirming this quality information, the buyer's side can determine the buying before the harvesting.

For the determination of the above calibration curve, the method by which the protein content rate is obtained is explained using the linear analysis as an example, the use of a non-linear analysis is also possible. Also, as a method for determining the calibration curve based on the chemically analyzed value and the correlation of the absorbency related thereto, there is a possibility of using a chemometrics technique. Also, although the quality has been based on the protein content rate, other grain component contents which can serve as factors for the judgement of the grain such as contents of starch, water and potassium, or as sensory factors such as taste or flavor, may be made quality factors. Especially, the above protein content rate is known as an important component value for determining the quality of the wheat so that, to use this as a quality factor in the wheat, ensures the quality of the wheat to be harvested. In the case of the rice, it is known that the yield is increased by the increase in the protein content rate but the taste is lowered, and the taste is improved by the decrease in the protein content rate but the yield is decreased. Thus, the protein content rate is an important component factor for the rice and wheat.

The measurement of a plurality of absorbencies as above requires that the wavelengths which respectively correspond to individual absorbencies be measured. As the wavelength regions, a plurality of wavelengths of a near infrared ray region or a visible ray region may be used. For producing the plurality of wavelengths, there are methods in which a plurality of narrow band optical filters in accord with wavelengths are used, a diffraction grating is used so as to enable the irradiation of light with intervals of several nanometers, or a sensor array having a special arrangement at the light receiving sensor side is utilized so that, without using the narrow band filters, an appropriate wavelength is selected from among a plurality kinds of wavelengths, and a plurality of absorbencies are measured.

The predetermined time mentioned above is made 40 days or 30 days prior to the harvesting in consideration of the reasons that it is desirable for the quality to be estimated as early a time as possible before the harvesting, and that, in grain plants, there is a trend for the amount of nitrogen in the leaf blade to stably and gradually decrease 30–40 days before the harvesting time, and this is the time when a change therein is small as compared with that at the fertilizing application stages (additional manuring and ear manuring). When the absorbency of the leaf blade is measured at this time, the quality estimation can be made most precisely. As to the final fertilization time in grain plants, it is most common that, in the case of rice, the fertilizer application is mostly finished 40 days prior to the harvesting time and, in the case of wheat, the fertilization is mostly finished 30 days prior to the harvesting time. This means that the time selected for the estimation is when the fertilization is finished and the amount of nitrogen in the leaf blade of the plant is not directly influenced by the fertilization. If the absorbency is measured subsequently (that is, between 30 days prior to the harvesting time and the harvesting), the estimation time is too late, and as information that can be drawn from the field, it is out-dated for both the producer's side and the buyer's side.

Figure 2:
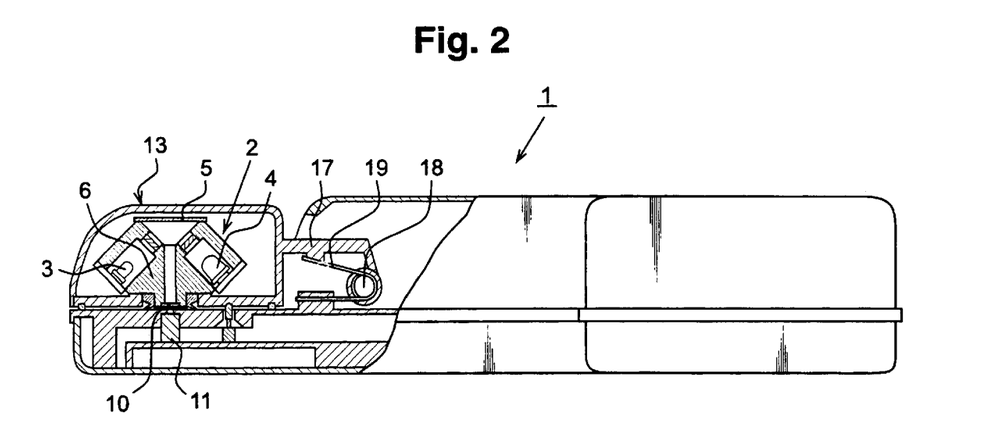
FIG. 2 is a side view, partly broken, of the main portion of the measurement device according to the invention.
Figure 3:
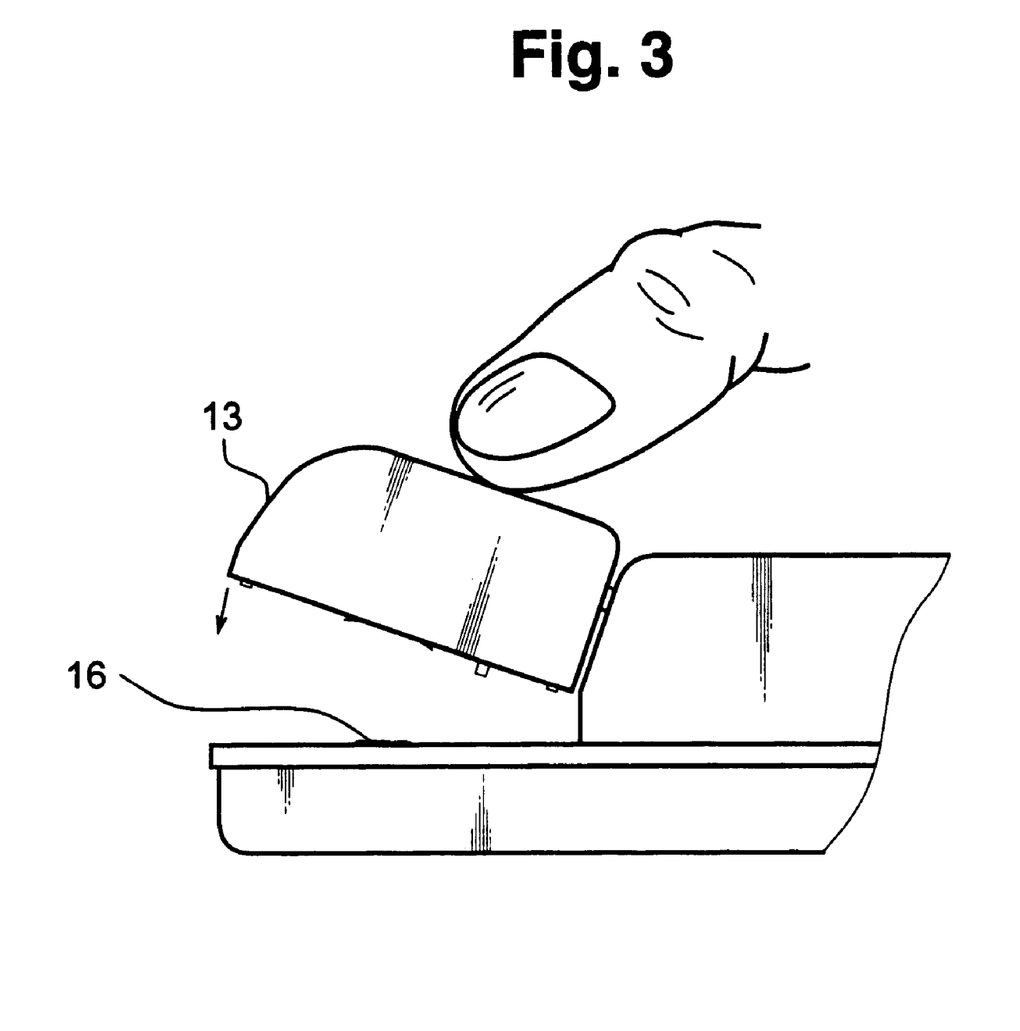
FIG. 3 is a side view of the measurement device, for showing the mode of using the same according to the invention.
Figure 4:
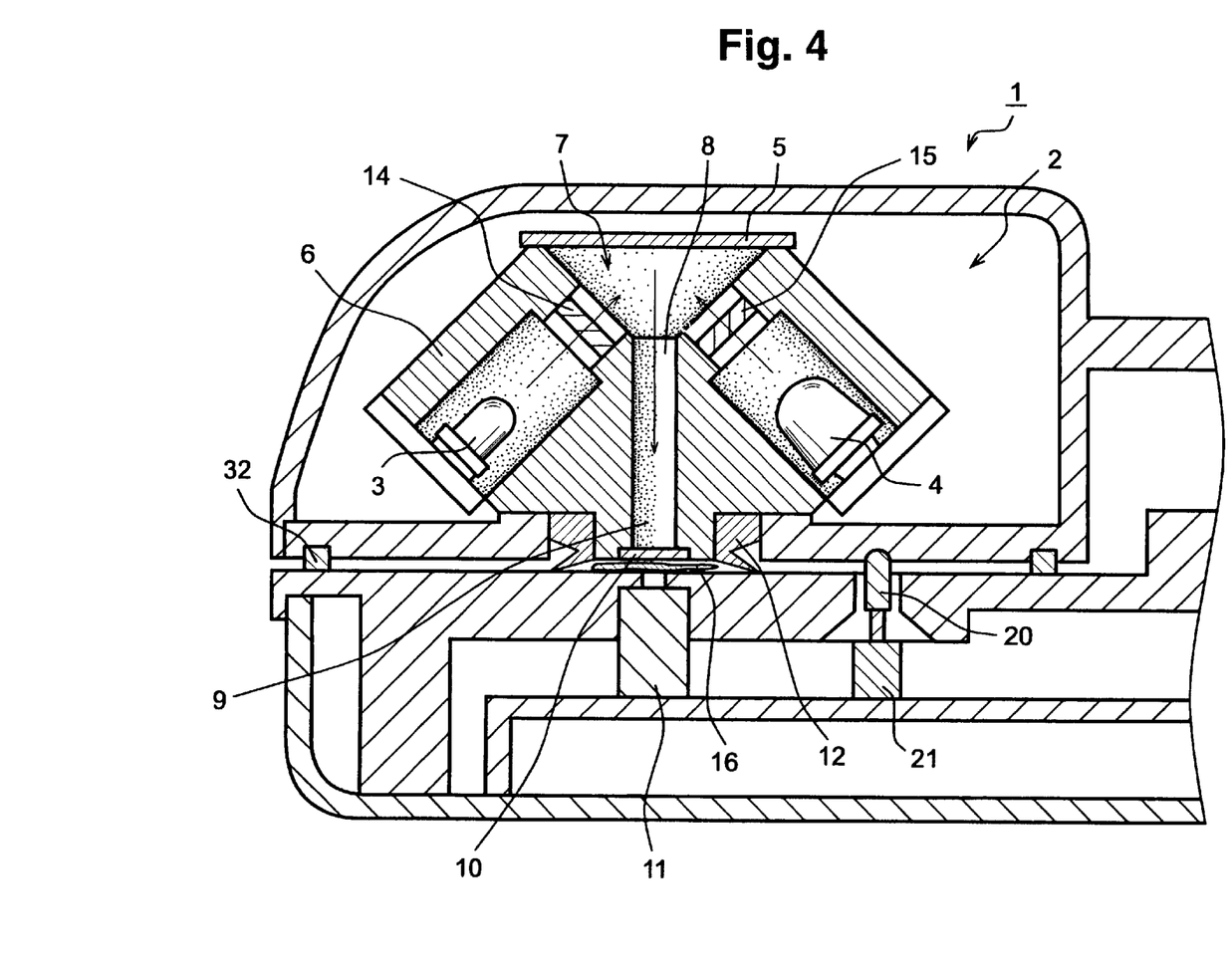
FIG. 4 is a side sectional view for showing the main portion of the measurement device according to the invention.

Now, a portable absorbency measurement device 1 as a preferred embodiment of the invention is explained with reference to FIGS. 2 to 5. FIGS. 2 and 4 show sectional views, partly broken, of the main portion of the portable measurement device 1. As shown in FIGS. 2 and 3, it is arranged that a main body 13 disposed at an upper portion is provided with a light source section 2 and a photodiode (not shown) which is a light amount detection device 11 disposed under the main body. In the light source section 2, there are provided, in the same circumference, a plurality of light emitting diodes (LEDs) 3, 4 which have different wavelength peaks, and narrow band filters having different passing wavelengths are provided respectively to the LEDs 3, 4. Preferred wavelength bands range from 500 nm to 1100 nm, and the selection is made from these wavelengths as to the narrow band filters 14, 15 having predetermined special wavelengths and having relation to the component targeted. Light emitted from each of the LEDs 3, 4 is turned to light of specific wavelength by the narrow band filters 14, 15 and is incident on a diffusion reflection plate 5 which reflects the light. Also, a block 6 is so arranged that the light from each of the LEDs 3, 4 is incident substantially in the same angle on the diffusion reflection plate 5.

The light reflected from the diffusion reflection plate 5 enters in a reflection light path 8 provided in the center of the block 6, and is incident on a diffusion transmission plate 10 provided at the radiating side 9 of the reflection light path 8. The diffusion transmission plate 10 is provided perpendicularly to the optical axis of the reflection light path 8, and is made of a frost glass or a milky white glass in a circular form. The diffusion transmission plate 10 may have a frost surface either on the radiating side 9 or on the measured leaf 16 side, or on both the sides. Further, the opening section 7 and the reflection light path 8 may preferably be formed by, for example, a solid aluminum. The inner surface of the aluminum may be processed so as to have a flecked effect, but the same effect can be obtained easily and at a low cost by using a Flon coating.

By repeating the reflection and the diffusion in the space surrounded by the opening 7, the reflection light path 8 and the diffusion reflection plate 5, the light comes out from the reflection light path 8 and is received by the light amount detection device 11 through the measured leaf 16 after passing through the diffusion transmission plate 10. Between the light amount detection device 11 and the diffusion transmission plate 10, there is fixedly provided a spacer 12 in a ring-like form which makes it possible to insert and fix a sample leaf with a space being provided.

Further, an upper periphery of the light source section 2 is provided with a cap 13, and an arm 17 extended from the cap 13 is held by an axis 18. The axis 18 holding the cap 13 carries a coil spring 19 so that the cap 13 is constantly urged upwardly. That is, as shown in FIG. 3, the performing of the measuring is ready when the leaf 16 to be measured is inserted and the cap 13 is pressed down. As to the timing of the measuring, when the cap 13 is pressed down, a press-down projection 20 provided under the cap 13 presses down a micro-switch 21 located at an opposing position. When the pressing down of the cap 13 is detected, the measuring (measuring of light irradiation and light amount) is conducted. Also, in a preferred form, the spacer 12 in a ring-like form made of a resilient material is provided to surround the diffusion transmission plate 10 so that, when the cap 13 is pressed down, the spacer 12 holds the sample leaf under pressure and produces the effect of shielding the outside light.

Figure 5:
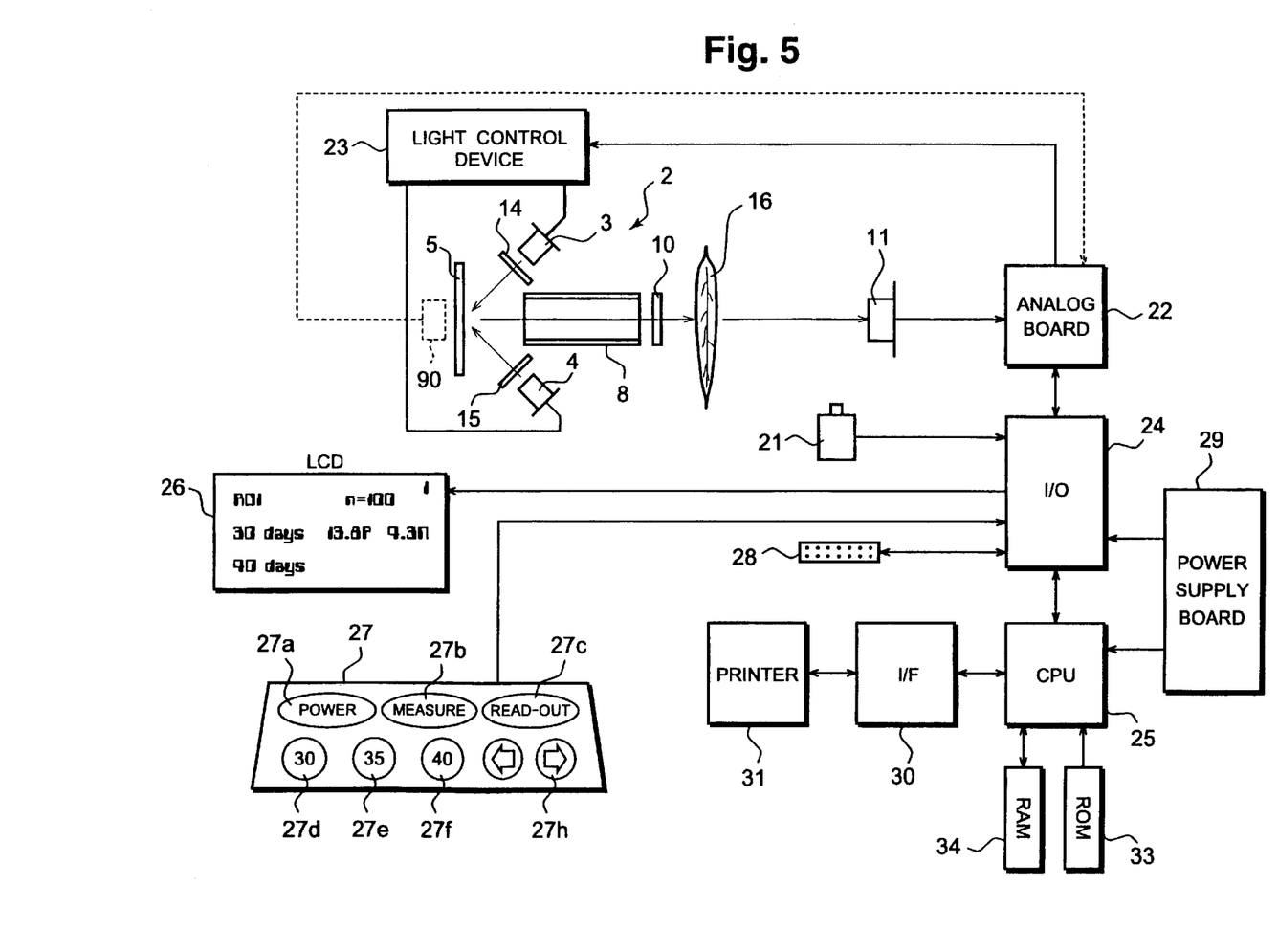
FIG. 5 is a block diagram for showing the processing of signals in the measurement device according to the invention.

Next, the absorbency measurement device 1 is explained with reference to FIG. 5 which shows the same in a block diagram. The amount of light transmitted through the sample leaf 16 to be measured at the measuring section consisting of the light source section 2 and the light amount detection device 11 is converted to an analog signal by the light amount detection device 11 and is communicated to an analog-board 22. With the light source section 2, there is provided a light emission control device 23 of the LEDs 3, 4. At the analog-board 22, either the A/D conversion from an analog signal to a digital signal, or the V/F conversion from a voltage to a frequency is conducted. The signal converted is inputted, through an I/O board 24, to the CPU board 25 which serves as the operation and control unit. The I/O board 24 is provided with a liquid crystal display device 26 for displaying a result of the measurement, a result of calculation or operational instructions, an input section 27 for operation, a connecting port 28 of an RS232C for inputting and outputting data to and from outside units, a switch 21, etc. The CPU board 25 and the I/O board 24 are connected to a power source board 29 for receiving a supply of power therefrom. Also, a printer 31 is connected to the CPU board 25 through a printer I/F board 30. Further, to the CPU board 25, there are connected a read-only-memory (hereinafter referred to as "ROM") 33 and a random access memory (hereinafter referred to as "RAM") 34. The ROM 33 stores a plurality of calibration curves on a field-to-field basis or on a variety-to-variety basis in the form of the Formula (1) or Formula (2) explained above. Further, the ROM 33 stores programs for performing the calculation of the quality with the protein content rate by measuring the absorbency at the absorbency measurement device 1, that is, a series of the programs from the measuring of the absorbency up to the calculating and displaying.

Figure 6:
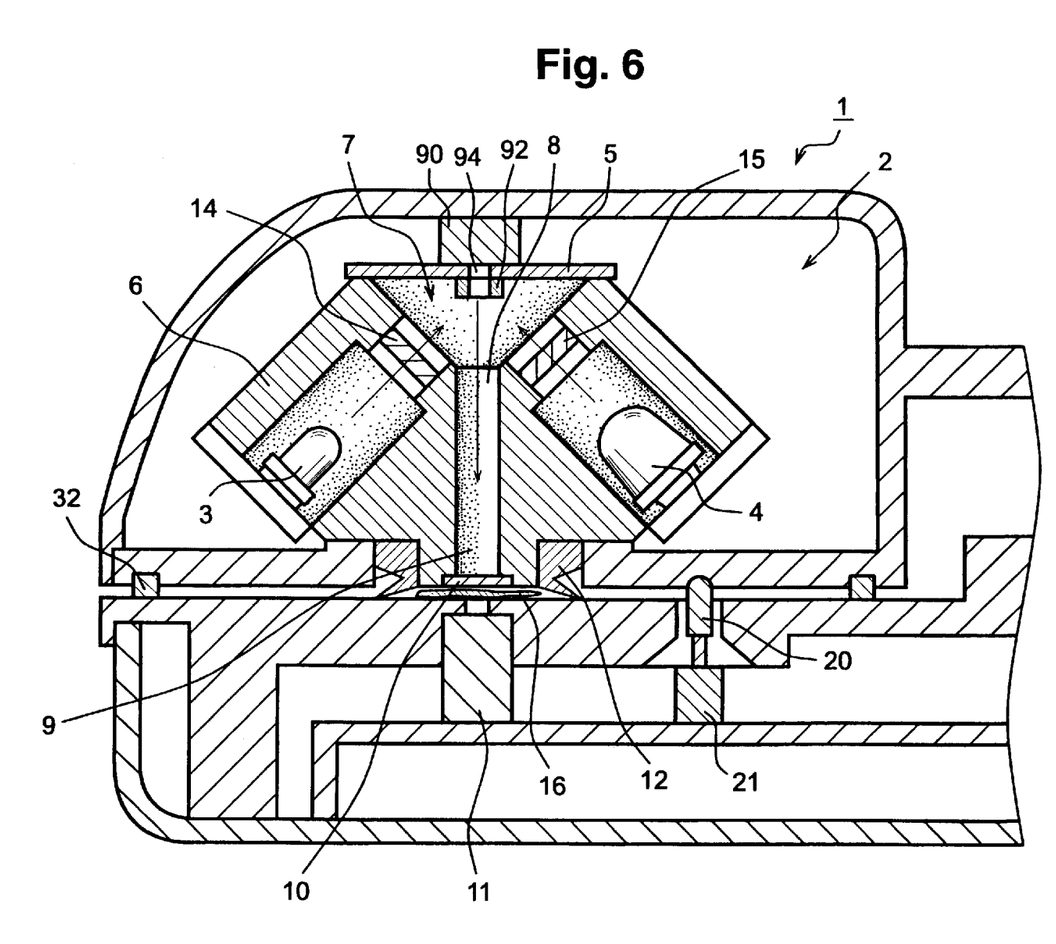
FIG. 6 is a side sectional view of the main portion of another example of the measurement device according to the invention.

So far the explanation has been for the measuring of the transmitted light of the sample leaf 16, but it is possible, as shown in FIG. 6, to arrange that an opening 94 is provided in the center of the diffusion reflection plate and, on the opening side of the diffusion reflection plate 5, a light shielding member 92 for preventing the entering of the direct light from the light sources 3, 4 is provided with the opening 94 being in the center, and the reflection light amount receiving means 90 is provided in alignment with the opening 94. This reflection light amount means 90 may also be connected to the analog board 22 so as to detect the transmission light amount and the reflection light amount together with the light amount detection means 11.

The function of the absorbency measurement device 1 constructed as above is hereinafter explained. When the sample leaf 16 is inserted into the absorbency measurement device 1 and the cap 13 is pressed down, a signal from the switch 21 is communicated to the CPU board 25 and, from the CPU board 25, a signal is sent to the light emission control device 23 so that the emission signal is sent to the light source 2 from the light emission control device 23. Thus, the light is irradiated on the sample leaf 16 alternately by the LED 3 and LED 4 in the light source 2. The light emitted from the LEDs 3, 4 turns to light of a specific wavelength in the near infrared ray region and the visible light region by the narrow band filters 14, 15, and since such light arrives at the light amount detection device 11 from the diffusion and transmission plate 10 after repeating the above explained reflection and diffusion, the sample leaf 16 receives the light uniformly in the same extent as when an integration-sphere is used.

When the sample leaf 16 is irradiated, the transmitted light or the reflected light is received by the light amount detection device 11 individually and correspondingly to the LEDs 3, 4, and the received light is communicated to the analog board 22 for A/D conversion. At the analog board 22, the A/D conversion is conducted, and the result is inputted into the CPU board 25 via the I/O board 24. At the CPU board 25, the transmissivity or the absorbency of light is calculated from the transmission light or the reflection light of the sample leaf 16, and the values resulted are stored in the RAM 34.

The input section 27 is provided with a power source switch 27a for switching the power for absorbency measurement device 1, a measurement switch 27b for enabling the transmission light measurement, a read-out switch 27c, having switching functions, for reading-out the calibration curve (formula) stored in the ROM 33 or the absorbency or transmitted light data stored in the RAM 34, the results of calculation or sample numbers, time setting switches 27d–27f for setting the measuring times of the transmitted light, and a selection switch 27h for selecting the displayed formula and values. The input section 27 is equipped with a quality estimation mode for measuring the transmitted light for estimating the quality after the harvesting, and a calibration preparation mode for measuring the transmitted light amount for preparing the calibration curve. The switching between these modes is effected such that the switching to the mode of quality estimation is by one push of the measuring switch and the switching to the mode of calibration curve preparation is by continuous push of the measuring switch 27b for a predetermined time (for example, 3 seconds). By pressing the read-out switch 27c, the items such as the calibration curve (formula) stored in the ROM 33, the absorbency data and the calculation results stored in the RAM 34, and sample numbers are displayed in a scroll form. The selection switch 27h allows the selection of the necessary data and formula from among the relevant data items displayed in the scroll form by scrolling them further by using a right arrow mark or a left arrow mark. When, after the selection, the read-out switch 27c is pressed again, the selected data or formula are displayed or set as necessary.

The liquid crystal display section 26 displays various items thereon, for example, "RO1" as the measuring sample No.; "n=100" as the number of samples; "30 days or 40 days before" as the predetermined times representative of the measuring times; "13.8P" as the protein content rates estimated at the respective predetermined times; and "4.3N" as the amount of nitrogen in the leaf blade. By further displaying the value "1" which represents the kind of the calibration curve presently used, the operator can easily confirm therefrom as to whether the calibration curve formula being used is suitable to the sample leaf 16. As to the predetermined time, this time is set 35 days prior to the harvesting at the input section 27 so that, similarly, the indication of 35 days may be added. In the column "40 days", the quality estimation value calculated based on the absorbency value obtained from the sample leaf 16 measured 40 days before the harvesting is displayed. In the column of "30 days", there may be displayed either the quality estimation value calculated based on the absorbency value obtained from the sample leaf 16 measured 30 days before the harvesting, or the quality estimation value obtained based totally on the absorbency values 40 days and 30 days before the harvesting. Also, as explained before, the item for "35 days" may be provided. As to the number of sample, when the measurement is made for preparing the calibration curve, the number of samples measured for the preparation of the calibration curve is displayed, and when the measurement is made for the estimation of the quality, the number of samples measured for the quality estimation may be displayed.

In the state in which the calibration curve is not being prepared, as already explained, the absorbencies of a plurality of samples, for example, 100 samples from one field or one variety, taken 30 days before the harvesting are measured and stored in the RAM 34. The absorbencies thus obtained are processed as shown in FIG. 1 for the preparation of the calibration curve. That is, 30 days after the measurement of the absorbency, the wheat particle, in the case of the wheat, matured from each wheat plant whose sample leaf 16 was measured for the absorbency, is subjected to the chemical analysis 36 and the measurement of the protein content rate is carried out for each sample absorbency. The protein content rate which is the chemical analysis value obtained is inputted into the personal computer 35 through a keyboard, and also the absorbencies of the 100 samples already stored are inputted in the personal computer 35 through the connecting port 28 of the measurement device 1. The subsequent procedures follow the same procedures as those used for preparing the Formula (1) explained before, and the calibration curve in which the constant was determined by the regression analysis is prepared by keeping the correlation between the protein content rate values and the absorbency values. The calibration curve thus prepared is fed back and stored in the ROM 33 of the absorbency measurement device 1.

Next, for the estimation of the quality, the absorbency of the sample leaf 16 currently growing and taken 30 days before harvesting is measured by the absorbency measurement device 1 and is stored in the RAM 34. When the absorbency stored in the RAM 34 is applied to the calibration curve, Formula (1), stored in the ROM 33 of the absorbency measurement device, the protein content rate after the harvesting is calculated and displayed at the liquid crystal display device 26 as, for example, "13.8P". It is normal that a plurality of absorbencies are stored with respect to one sample. In the present example, the absorbencies result from each of the light sources 3, 4 and they are stored in series with the sample numbers being attached. By increasing the number of light sources or by enabling to exchange filters 14, 15, it is possible to increase the number of absorbencies with respect to one sample. In this case, if the calibration curve for calculating the amount of nitrogen in the leaf blade is stored in advance in the ROM 33, it is possible to calculate the amount of nitrogen in the leaf blade based on the absorbency which had been stored in the RAM 34, and the liquid crystal display device 26 can display as, for example, "4.3N" in addition to the displaying of the protein content rate.

When the measurement of the absorbency of the sample leaf 16 is to be made twice, that is, 40 days and 30 days before the harvesting, the following events take place. In the state in which the calibration curve has not been prepared, from one field or one variety, a plurality of sample absorbencies 40 days before the harvesting, for example, 100 samples, are measured and stored in the RAM 34. As the growth of the plant progresses, a plurality of sample absorbencies 30 days before the harvesting are measured in the same manner as in 40 days before the harvesting, and are stored similarly in the RAM 34. On the day 30 days afterward from the day on which the absorbency 30 days before the harvesting is measured, the wheat particles, as the case may be, obtained after the maturing of each plant whose sample leaf 16 was measured for the absorbency, are subjected to the chemical analysis 36 for the individual sample absorbencies, and the respective protein content rates are measured. The protein content rates which are the values of the chemical analysis thus obtained are inputted to the personal computer 35 from the keyboard, and the sample absorbencies of 100 samples 40 days and 30 days before the harvesting, which are stored previously, are inputted in the personal computer 35 through the connecting port 28 of the measurement device 1. Hereinafter, by following the same procedures as for preparing the Formula (2) explained before, with the correlation being kept between the protein content rates and the absorbencies, the constants are determined by the regression analysis, whereby the calibration curve is prepared. The calibration curve thus prepared is fed back and stored in the ROM 33 of the absorbency measurement device 1.

For the estimation of the quality, the absorbency of the sample leaf 16 currently growing and taken 40 days and 30 days before harvesting is measured by the absorbency measurement device 1 and is stored in the RAM 34. When the absorbency stored in the RAM 34 is applied to the calibration curve, Formula (2), stored in the ROM 33 of the absorbency measurement device, the protein content rate after the harvesting is calculated and displayed at the liquid crystal display device 26 as, for example, "13.8P". The value obtained here is not a value obtained by calculating and averaging the protein content rates independently of the absorbency values 40 days and 30 days before the harvesting. In the value, the changes in the absorbencies in two times are taken into account as when the constants were determined by multiple regression analysis in preparing the calibration curve, Formula (2), so that the calibration curve can cope with changes in the growth caused by environmental changes.

In the liquid crystal display device 26, both the items "30 days" and "40 days" may be provided and, additionally, the calibration curve may be stored in the ROM 33, not only as the Formula (1) for 30 days and the Formula (2) for 30 days and 40 days, but also as a Formula (3) for 40 days. In this way, the liquid crystal display device 26 may display, as "40 days", the estimation value of the protein content rate measured 40 days before harvesting, and additionally displays, as "30 days", the estimation value of the protein content rate measured 30 days before the harvesting, thus enabling the visual confirmation of changes in the protein content rates in the independent estimation values 40 days before and in the independent estimation values 30 days before. Also, from the Formula (2), it is possible to estimate the protein content rate at the harvesting totally from both the absorbencies 30 days and 40 days before.

Incidentally, when the calibration curve is prepared or the quality after the harvesting is estimated, the sample leaf 16 is specified from the leaves of the plant in growth, and this leaf is inserted in the measurement device in such a way that the leaf 16 is measured without being destructed. The sample leaf is not taken off from the plant for the measurement so that the subsequent growth of the plant is not affected. The correlation between the transmitted light amount and the quality estimated from such transmitted light amount can be maintained unchanged from the time the calibration curve was prepared so that the quality can be estimated with high precision.

In preparing the calibration curve, the leaf blade information 30–40 days prior to the harvesting and the quality value information after the harvesting are obtained from the same stalk of the plant without the plant being affected, it has become possible to prepare the calibration curve and to estimate the quality with the precision being ensured both for the preparation of the calibration curve and for the quality estimation after the preparation of the calibration curve.

After the preparation of the calibration curve, the result of the measurement can be confirmed on the spot, so that it has become possible to conduct the quality estimation without the need of a complicated process such as chemical analysis. The confirmation of the value can be made in the field so that it is made possible to provide the information to a third party on the spot. Also, if the output device is provided, the values may be provided readily to the third party. Therefore, the precision in the judgement on the part of the buyers is enhanced, and the producers can provide assurance for the quality whereby the buyers can make the buying without hesitation.

While the invention has been described in its preferred embodiments, it is to be understood that the words which have been used are words of description rather than limitation and that changes within the purview of the appended claims may be made without departing from the true scope of the invention as defined by the claims.

What is claimed is:

1. A method for estimating a quality of grains to be harvested from a grain plant in the future, during a growth period prior to the harvesting, said method comprising the steps of:

establishing a quality conversion coefficient for estimating a specific quality of grains after the harvesting based on absorbencies relating to the specific quality of the grains obtained by irradiating light having predetermined wavelength regions on a leaf of a grain plant in growth at a predetermined time during the growth period of the grain plant and the specific quality obtained from the same grains after the harvesting; and estimating the quality of the grains to be harvested in the future based on said quality conversion coefficient and absorbencies relating to said specific quality obtained from a leaf of the grain plant presently growing at the predetermined time.

2. A method for estimating a quality of grains according to claim 1, said quality conversion coefficient is obtained totally from respective absorbencies at a plurality of predetermined times during the growth period of the grain plant and the specific quality obtained from the same grains after the harvesting, and the quality of the grains to be harvested is estimated totally based on said quality conversion coefficient and the respective absorbencies relating to said specific quality obtained from the leaf of the grain plant presently growing at said plurality of predetermined times.

3. A method for estimating a quality of grains according to claim 2, in which said qualities of the grains estimated at the different predetermined times are displayed simultaneously.

4. A method for estimating a quality of grains according to claim 1, in which said specific quality relates to the amount of protein.

5. An apparatus for estimating a quality of grains to be harvested from a grain plant in the future, during a growth period prior to the harvesting, said apparatus comprising:

a light source means for irradiating light having predetermined wavelength regions on a leaf of a grain plant;

a light receiving means for receiving at least one of transmission light and reflection light obtained by irradiating light on the leaf of the grain plant presently growing from said light source means;

a storing means for storing a quality conversion coefficient for estimating a specific quality of the grains after the harvesting, said quality conversion coefficient having been calculated from absorbencies obtained by irradiating light on a leaf of a grain plant in growth at a predetermined time during the growth period of the grain plant and the specific quality obtained from the same grains after the harvesting;

a calculating means for calculating the quality of the grains from said quality conversion coefficient and the absorbencies converted from the received amount of light obtained by said light receiving means from the leaf of the grain plant presently growing at the predetermined time; and a display means for visually displaying the results of the calculation made by said calculating means.

6. An apparatus for estimating a quality of grains according to claim 5, in which said storing means stores a quality conversion coefficient for estimating the specific quality of the grains after the harvesting, said quality conversion coefficient having been calculated totally from the respective absorbencies obtained by irradiating light on the leaf of the grain plant in growth at a plurality of predetermined times, and the specific quality obtained from the same grains after the harvesting, said storing means further storing the respective received amounts of light or the respective absorbencies converted from the received amounts of light, obtained by irradiating light on the leaf of the grain plant presently growing at the plurality of predetermined times and, in which, said calculating means converts the amount of the light received from the leaf of the grain plant presently growing at the plurality of predetermined times into the absorbencies, and the quality of the grains to be harvested in the future is calculated totally based on said absorbencies and said quality conversion coefficient.

7. An apparatus for estimating a quality of grains according to claim 6, in which said display means arranged such that the qualities of the grains estimated at the different predetermined times are displayed simultaneously.

8. An apparatus for estimating a quality of grains according to claim 5, in which said specific quality relates to the amount of protein.

\* \* \* \* \*

UNITED STATES PATENT AND TRADEMARK OFFICE
CERTIFICATE OF CORRECTION

PATENT NO. : 6,208,420 B1
DATED : March 27, 2001
INVENTOR(S) : Satoru Satake, Yukio Hosaka, Hideharu Maruyama, Nobuhiko Nakamura, and Nobuharu Yagishita It is certified that error appears in the above-identified patent and that said Letters Patent is hereby corrected as shown below:

Column 4,
Line 41, "content tent" should be -- content --.

Signed and Sealed this

Sixth Day of November, 2001

Attest:

NICHOLAS P. GODICI
Attesting Officer    Acting Director of the United States Patent and Trademark Office